(12) United States Patent
Beck

(10) Patent No.: US 9,608,978 B2
(45) Date of Patent: *Mar. 28, 2017

(54) RELATIONSHIP-BASED AUTHORIZATION

(71) Applicant: Medox Technologies, Inc.

(72) Inventor: Michael Beck, New York, NY (US)

(73) Assignee: Medox Technologies, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/072,797

(22) Filed: Mar. 17, 2016

(65) Prior Publication Data

US 2016/0205104 A1 Jul. 14, 2016

Related U.S. Application Data

(63) Continuation of application No. 14/444,142, filed on Jul. 28, 2014, now Pat. No. 9,325,692, which is a
(Continued)

(51) Int. Cl.
*H04L 9/32* (2006.01)
*H04L 29/06* (2006.01)
(Continued)

(52) U.S. Cl.
CPC ............ *H04L 63/08* (2013.01); *G06F 19/322* (2013.01); *G06F 21/31* (2013.01); *G06F 21/33* (2013.01);
(Continued)

(58) Field of Classification Search
CPC .......... G05F 21/33; G05F 21/31; G05F 21/30; G05F 21/6245; G05F 21/6272; H04L 63/10; H04L 63/08
See application file for complete search history.

(56) References Cited

U.S. PATENT DOCUMENTS 6,516,315 B1 * 2/2003 Gupta ................. G06F 21/6218
7,100,206 B1 8/2006 Pere
(Continued)

OTHER PUBLICATIONS

Written Opinion of the International Searching Authority for PCT/US07/09008, mailed Mar. 19, 2008.

*Primary Examiner* — Saleh Najjar
*Assistant Examiner* — Devin Almeida
(74) *Attorney, Agent, or Firm* — Mintz Levin Cohn Ferris Glovsky and Popeo, P.C.

(57) ABSTRACT

Methods and apparatus, including computer program products, related to relationship-based authorization. In general, data characterizing a request for authorization to a computer-based resource is received, and the authorization may be provided based on one or more relationships of a requesting principal. A determination may be made as to whether a requesting principal is authorized, which may include determining whether the requesting user has a relationship with a principal that has management rights of the computer-based resource and determining whether the relationship allows for an access, such as a use of the computer-based resource, if the requesting principal has a relationship with the other principal. If there is no such relationship, a determination may be made as to whether an organization of the requesting principal has a relationship with the other principal that allows for the access.

26 Claims, 5 Drawing Sheets

Related U.S. Application Data continuation of application No. 11/786,486, filed on Apr. 11, 2007, now Pat. No. 8,793,768.

(60) Provisional application No. 60/791,289, filed on Apr. 11, 2006.

(51) Int. Cl.
  *G06F 19/00* (2011.01)
  *G06F 21/33* (2013.01)
  *G06F 21/62* (2013.01)
  *G06Q 50/22* (2012.01)
  *G06Q 50/24* (2012.01)
  *G06F 21/31* (2013.01)

(52) U.S. Cl.
  CPC ...... *G06F 21/6245* (2013.01); *G06F 21/6272* (2013.01); *G06Q 50/22* (2013.01); *G06Q 50/24* (2013.01); *H04L 63/10* (2013.01)

(56) References Cited

U.S. PATENT DOCUMENTS

| | | |
|---|---|---|
| 7,181,017 B1 | 2/2007 | Nagel et al. |
| 2002/0010679 A1 | 1/2002 | Felsher |
| 2003/0046564 A1 | 3/2003 | Masuda et al. |
| 2003/0167392 A1 | 9/2003 | Fransdonk |
| 2003/0216943 A1 | 11/2003 | McPhee et al. |
| 2004/0122790 A1 | 6/2004 | Walker et al. |
| 2005/0165627 A1 | 7/2005 | Fotsch et al. |
| 2005/0197860 A1 | 9/2005 | Joffe et al. |
| 2006/0004588 A1 | 1/2006 | Ananda |
| 2006/0010324 A1 | 1/2006 | Appenzeller et al. |
| 2006/0229911 A1 | 10/2006 | Gropper et al. |
| 2007/0005396 A1 | 1/2007 | Lee |
| 2007/0006322 A1 | 1/2007 | Karimzadeh et al. |
| 2007/0143215 A1 | 6/2007 | Willems |

\* cited by examiner

RELATIONSHIP-BASED AUTHORIZATION

CROSS REFERENCE TO RELATED APPLICATIONS

This application is a continuation application of U.S. patent application Ser. No. 14/444,142, filed Jul. 28, 2014 which is a continuation of U.S. patent application Ser. No. 11/786,486, filed Apr. 11, 2007, and granted as U.S. Pat. No. 8,793,768, which claims the benefit of U.S. Provisional Patent Application entitled "Trusted Third Party Authorization," filed Apr. 11, 2006, Application Ser. No. 60/791,289, the contents of each of which are hereby fully incorporated by reference.

BACKGROUND

The present disclosure relates to data processing by digital computer, and more particularly to relationship-based authorization.

In general, information may be stored at a directory of a computer system, such as a personal computer or server computer system of a landscape of computers. A directory may store information about principals, such as users, organizations and systems, and computer-based resources. The scope of directory may be such that the directory may account for resources across an enterprise. For example, a company may implement a directory to store entries for first and second principal accounts, where an entry for the first account includes an electronic mailing address, telephone number, and the like for a first account and an entry for the second account includes similar information for that account. The electronic mailing address and telephone number may be considered attributes for those principals and the entries for those principals may be associated with the company that has implemented the directory.

A directory may store credentials used to authenticate a principal with the enterprise implementing the directory. Credentials may be in the form of a password, an issued authentication token (e.g., two-factor authentication token), biometric authentication characteristic data (e.g., data characterizing or summarizing the expected result of a biometric authentication of a principal), or other information that can be referenced to identify a principal desiring authentication by the implementing enterprise as known and, therefore, trusted.

Services may be used to perform authentication or authorization, or otherwise retrieve information from a directory regarding mentioned entity in accordance with a protocol. For example, Lightweight Directory Access Protocol (LDAP) is a protocol for accessing information from a directory of enterprise information. In general, accounts and associated information are organized hierarchically. For example, a company may set up a directory of its employees where the company might be considered a parent to the employees. In addition, information associated with each employee account may be organized hierarchically for each employee.

SUMMARY

The subject matter disclosed herein provides methods and apparatus, including computer program products that implement techniques related to relationship-based authorization.

In one aspect, data characterizing a request for authorization to access a computer-based resource by a requesting principal is received, a determination is made as to whether the requesting principal is authorized for the access to the computer-based resource, and authorization is provided if the requesting principal is authorized for the access. The determining may include determining whether the requesting principal has a relationship with a principal that has management rights of the computer-based resource, and determining whether the relationship allows for the access to the computer-based resource if the requesting principal has a relationship with the principal that has management rights of the computer-based resource. If there is no such relationship, a determination may be made as to whether an organization of the requesting principal has a relationship with the principal that has management rights of the computer-based resource that allows for the access.

In a related aspect, data characterizing a request for authorization to access a computer-based resource is received, a determination is made as to whether a requesting principal is authorized for the access, and authorization is provided for the requesting principal if the requesting principal is authorized. The determining may include determining whether the requesting principal has an implicit or explicit relationship with a principal, where the relationship indicates the requesting principal has access rights.

In a related aspect, data characterizing a request for authorization to access a computer-based resource is received, a determination is made as to whether a requesting principal is authorized for the access, and authorization is provided for the requesting principal if the requesting principal is authorized. The determining may include determining whether the requesting principal has a user to user or user to organization relationship with a principal, where the relationship indicates the requesting principal has access rights.

In a related aspect, data characterizing a request for access to computer-based resource by a first principal is received, a determination is made as to whether the first principal is authorized for the access to the computer-based resource, and authorization is provided if the requesting principal is authorized for the access. The determining may include determining whether the first principal has a first relationship with a second principal that has management rights of the computer-based resource based on a query of one or more data structures comprising user to user relationships between principals being users. The determining whether the first principal is authorized may further include determining whether the first relationship allows for the access to the computer-based resource based on properties of the first relationship if the first principal has the first relationship, and, if not determining whether an organization of the first principal has a second relationship, with the second principal, that allows for the access. Determining whether the organization has the second relationship may be based on user to organization relationships and organization to user relationships of the data structures.

The subject matter may be implemented as, for example, computer program products (e.g., as source code or compiled code), computer-implemented methods, and systems.

Variations may include one or more of the following features.

A principal may be a user, organization, component of a computer system, or a computer system.

A computer-based resource may be a type of information, such as content.

Authorization to access a computer-based resource may include authorization to access, manage, or otherwise use a computer-based resource.

Management rights may include rights to manage access to, including use of, computer-based resources.

A relationship may indicate that a requesting principal has access rights based on an existence of the relationship or attributes associated with the relationship.

An access may be performed in response to receiving an authorization to perform the access.

Determining whether a principal is authorized to perform the access may include determining if in accordance with rules, roles, attributes, or some combination of those associated with a relationship a principal is authorized to perform the access. Roles may be assigned implicitly or explicitly. For example, a user may be a data content recipient by virtue of requesting access to a computer-based resource.

Relationships may be stored in a table such that a graph of relationships is described. A graph may include at least one child node of relationships having multiple parent nodes. A table may be a computer-based resource, a data store, a database, or another combination of program and/or memory such that social distance calculations may be performed during an authorization process and the like. The graph may include a case of at least one child node of relationships having a single parent node, and a direct relationship to another node that is neither its parent or descendent (e.g., a sibling node or the child node of another parent, and the like). The data structures may be non-hierarchical. The relationships of the data structures may be non-directed or directed.

Determining whether a requesting principal is authorized and has a relationship with a second principal, and determining whether an organization of the requesting principal has a relationship with the user that has management rights of the computer-based resource may be performed with reference to one or more data structures describing relationships between principals (e.g., users and users; users and organizations; organizations and users; organizations and organizations; users and systems; organizations and systems; systems and resources; and the like).

A principal having management rights of a computer-based resource (e.g., health-related content) may be a data content subject about whom the computer-based resource relates (e.g., patient).

A requesting principal may have access rights (e.g., be authorized) based on a relationship with a principal having management rights at a first time but might not have a access rights at a second time being later than or earlier than the first time based on a modification of the relationship, associated attributes, or both.

Relationships between principals may be associated with one or more attributes. At least one of the attributes may describe one or more of a time interval of a relationship, types of computer-based resources authorized for a relationship, types of authorized access, relevant identifiers used to communicate the relationship as unique per a pairing of principals, and current activity of a relationship.

Receiving data and determining whether a principal is authorized may be performed at a server. Access, usage, or management tasks of computer-based resources to which a principal has been authorized may be performed at a client.

A request may be a request for authorization to access of health information in a healthcare administrative, clinical, or non-traditional environment. Health information may include clinical information or administrative information regarding the delivery or receiving of care.

A requesting principal may be authorized for types of access of computer-based resources different from types of access authorized for another principal.

Data structures supporting storage of relationships may be one or more tables (e.g., logical or physical tables). The tables may be part of a computer-based resource, data source, database, memory, and/or configuration. Data structures may be facilitated using an assistance of a combination of a hierarchical directory and other mechanisms for relationship storage.

Data structures, given a time-phase and source node of reference to provide context, may be used to mimic a strict, hierarchical directory structure having a one to many cardinality between organizations and users. Protocols available for accessing such directories (e.g., LDAP) and applications for those structures (e.g., authentication, authorization, identity management, and the like) may be supported by an implementation of these structures.

A principal may be authenticated using credentials sent by a principal. The credentials may be used to identify the principal and relationships of the principal. The credentials may provide for authentication during a secure session.

Roles, rules, access rights and other attributes that may be associated with a relationship may determine authorization. Determining the authorization may include using specific characteristics (e.g., attributes, traits, or preferences) that are assigned to a principal characteristics or security policies explicitly specified for the requested computer-based resource, or characteristics of the owner, custodian, or subject of the requested computer-based resource.

Default behaviors for authorizing users, organizations, or systems to access health information may be specified, for example, through a user interface. Default behaviors may be available as default settings in a user interface, such as that of a mobile phone or website, where a user may specify recipients who may require access to health information.

Determining whether a principal is authorized for a computer-based resource may include reviewing any number of relationships, including different types of relationships (e.g., differences based on types of principals, such as user to user; differences based on hierarchy of principals, such as parent to child, sibling, and the like), and associated attributes. In addition, rules may be associated with scenarios and those rules may be used to determine authorization. As examples, while there might not be an explicit relationship between a principal being a data content recipient (e.g., a physician) and a data content subject (e.g., a patient) that expresses a preference for the way that a principal may be authorized to access a resource (e.g., the case where a patient is admitted for emergency care and has no prior relationship with the physician), a current employer (e.g., a hospital where the doctor is providing emergency treatment) of the requesting principal may have a relationship with the data content subject (e.g., the hospital may be a facility where the patient has received care in the past and therefore its staff is granted by the patient general access to information including allergies, medications, and the like) or a principal with whom the data content subject has a relationship preference (e.g., the patient's insurance company), may have an explicit or implied rule for the given context (e.g., an emergency, a regular visit, etc), such that authorization is provided. Determining whether an implicit relationship exists based on a combination of relationships or associated attributes, such as a scenario, may be referred to as determining whether a relationship exists based on social distance (e.g., determination of immediate and active affiliation with another principal).

The subject matter described herein can be implemented to realize one or more of the following advantages. Management of computer-based resources (including information or content), such as provision of computer-based resources or access to computer-based resources (including, computer-based resources shared across multiple devices; e.g., resources available on a network of computers where authentication and authorization to a network may require authentication and authorization similar to that expressed for a single computer-based resource), may be based on relationships, such as relationships of a principal requesting computer-based resources with other principals, such as users, organizations, systems, and the like. Advantageously, a context of a relationship may be used to determine computer-based resources or access to computer-based resources that may be provided. Relationships may be similar or the same as a graph such that a strict hierarchy, such as a tree-based hierarchy, need not be used. A child node of a graph or of a combination of relationships may have multiple parent nodes. Similarly a child node of a parent may have a direct relationship with the child node of another parent or sibling of the same parent. Relationships may include temporal attributes such that historic attributes of relationships may be maintained. For example, in a healthcare environment, patient information or access to patient information may be provided based on relationships, which may advantageously take into account features of such an environment, such as an existence of a principal beyond their relationship with organizations, such as an employer or insurance company; and, affiliations of insurance companies (e.g., attributes of relationships may be automatically inherited by affiliated principals, using techniques such as determining whether an existence of a social distance of the identified affiliation). Principals may have one or more roles and an assignment of roles may depend on a relationship. For example, rather than limiting a principal to a specific role which may be uniformly enforced with regard to all computer-based resources, user to user relationships may allow a principal to serve as custodian, owner, or subject of a computer-based resource and provide a context that determines authorization independent of other roles that may be assumed in different relationship contexts.

Details of one or more implementations are set forth in the accompanying drawings and in the description below. Further features, aspects, and advantages will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
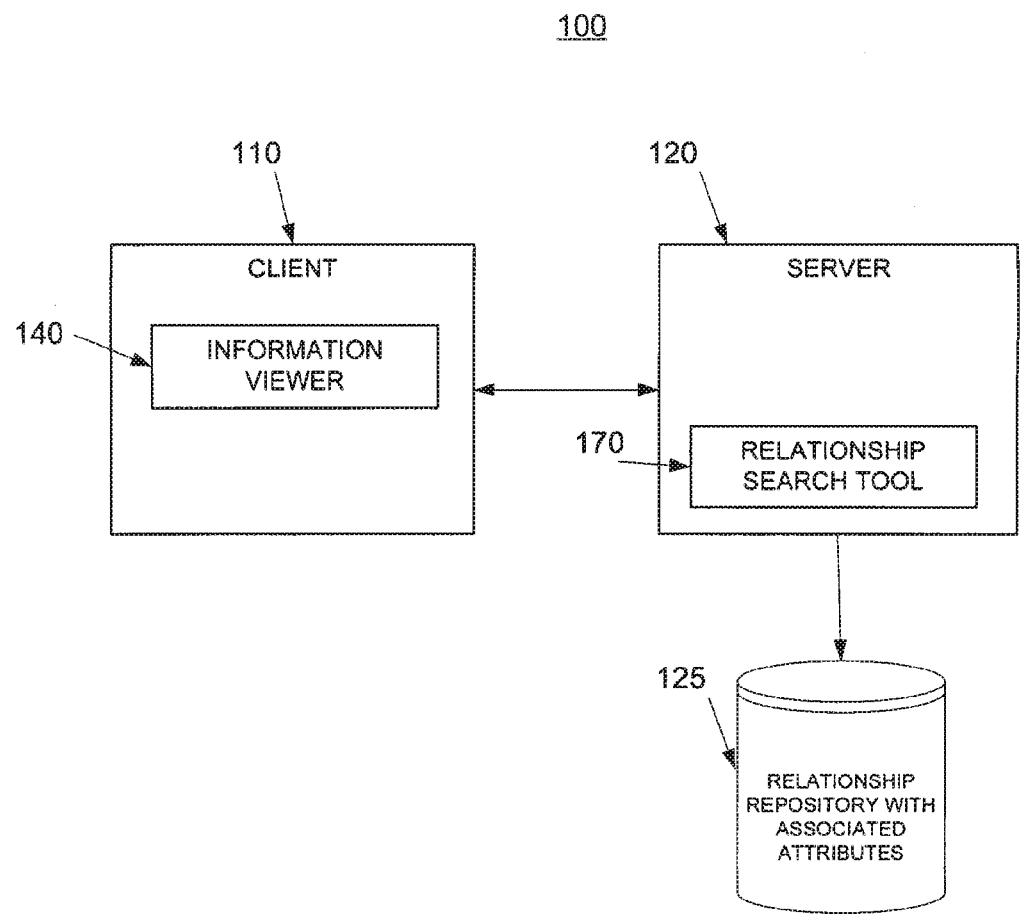
FIG. 1 is a diagram of a system to provide relationship-based authorization.
Figure 2:
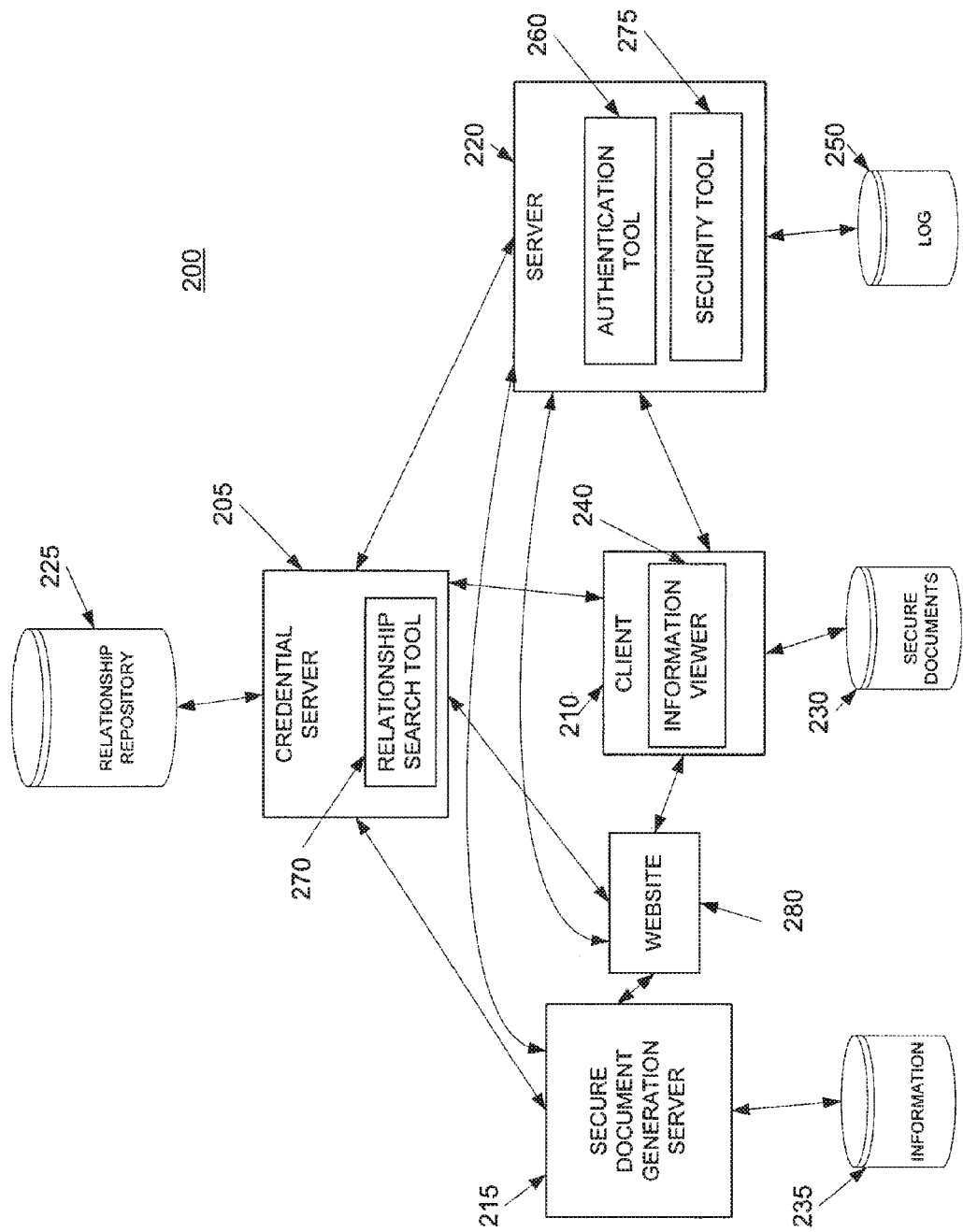
FIG. 2 is a diagram of a system to provide access and usage rights to computer-based resources based on relationship context.

In general, the systems 100, 200 of FIGS. 1, 2 may provide a client access to computer-based resources from a server and the information accessible to the client may depend on relationships between principals, such as a relationship of a principal of the client to a principal who is owner, custodian, or subject of the computer-based resources. Computer-based resources may include files, documents, content, data, system-provisions, computer-based resources, applications, application features, information, and the like. Principals may be users, such as individual users or users of an organization, or organizations that have accounts associated with either of the systems 100, 200.

In the systems 100, 200, there may be a number of relevant party roles, and a principal requesting authentication and authorization may be assigned zero or more of the roles to access, use, or manage the specified computer-based resource (e.g., a principal with no roles might not be allowed access). Roles may be assigned in a variety of scenarios, such as trust of a principal; trust of a principal's credentials in seeking authentication and authorization; physical location or proximity of a principal seeking authentication and authorization from a computer-based resource; and the like. The roles given a principal may include: data content subject, a role describing a principal about whom data is being shared (e.g. in a health information environment, it may be a patient); data content recipient, a role describing a principal who is seeking access to information regarding one or more data content subjects (the data may be packaged in a secure document, 'secure container' or 'secure container holding' as will be described below); data custodian, a role describing an owner of a source of information regarding a data content subject (e.g., in a health information environment, a doctor's office, hospital, or insurance company may have this role), which may be required by regulation or responsibility to log or control access to that information; data publisher, a role describing an aggregator of information regarding one or more data content subjects, who may additionally be a data publisher; relationship administrator, a role describing someone who represents a governing entity responsible for maintaining, or creating data content subject, data content recipient, and data custodian accounts (e.g., in a health information environment, an employer's group benefit's administrator or an insurance company's product contract group); and, a role describing a system administrator, who at a more supreme level may manage relationships (e.g., relationships between data subjects and data content recipients) and accounts (e.g., information about a data content subject or data content custodian in the systems 100, 200). The above party roles may be explicit or implicit, and may be combined with other types of roles. For example, a doctor may be assigned roles of a data content recipient and a doctor role, where the data content recipient role is implicitly assigned based on a request for a computer-based resource and the doctor role is explicitly assigned based on an attribute associated with a relationship of a patient with the doctor. In some implementations a program may be a user that has one or more roles. For example, a program may be a data content recipient and may request data in either of the systems 100, 200 of FIGS. 1 and 2.

In some implementations party roles may have variances. For example, there may be a distinction between a data content owner and data content custodian. For example, a data content subject may be a data content owner, and a data content custodian may have care over content or information of the data content owner. For example, in one system an insured party may be a data content subject and data content owner, where an insurance company of the insured party is the data content owner; however, in another system, an insured party may be a data content subject but not a data content owner, and, an insurance party may be the data content owner and data content custodian.

FIG. 1 is a diagram of a system 100 to provide relationship-based authorization. The system 100 includes a client 110, a server 120, and a relationship repository 125 of principals, relationships and associated attributes. In general, the client 110 may request information or authorization to access, use, or manage information from the server 120, which may use the relationship repository 125 to determine a response based on the relationship and related attributes stored at the relationship repository 125.

In general information includes computer-based resources and may include data, such as electronic mail addresses, telephone numbers, and the like, and, information may more particularly include content, such as audio, image, binary, and text files. Information may include the output of computer-based resources, including computer software, enterprise software systems, features of computational executables distributed over a local area network or wide area network. Information may include the metadata or attributes associated with information or network-based resources. In some implementations, the information may be secure documents or components of secure documents, as discussed with reference to FIG. 2.

As an example of operation of the system 100, the relationship repository 125 may include relationships of data content subjects and data content recipients, and information about data content subjects, such as addresses, that are attributes associated with relationships. Following that example, the client 110 may request an address of a data content subject by sending a request to the server 120. The server 120 may receive the request and perform a search of the relationship repository 125 using a relationship search tool 170 to find direct or indirect relationships between the data content recipient of the client 110 and the data content subject. If a relationship is found, attributes specifying an address may be used to form a response to the client 110. If a relationship is not found, a response may be returned that indicates no relationship exists.

As attributes may be associated with a relationship, rather than a principal that is data content subject, data content owner, or data content custodian of the requested information, a context of a relationship between the requesting principal may be used to provide different information. For example, a first relationship with a first data content recipient may have different attributes than attributes associated with a second relationship with a second data content recipient. For example, a private, personal electronic mailing address may be associated with a relationship between a data content subject and a friend being a data content recipient; whereas, a public, work electronic mailing address may be associated with a relationship between a data content subject a business client being a data content recipient.

The client 110 may be a tool or application program to send requests for information or access to information to the server 120. For example, the client 110 may include a graphical user interface with a text box for entering search criteria, such as a name of a data content subject and specific information desired about the data content subject, for searching the relationship repository 125. The client 110 includes an information viewer 140, which may be used to view information, such as a response, from the server 120. For example, the information viewer 140 may display contact information of data content subjects.

The client 110 may be a credentialed principal or used by a credentialed principal (e.g., a program may be a credentialed principal). In some implementations, a principal need not be credentialed and may have characteristics of a principal, such as being a person, organization, or system. A credentialed or uncredentialed principal may be considered "trusted" on a basis of information requested for authorization to access, use, or manage. The client 110 or its user might not be credentialed in cases where use, access, or management of information does not require authentication for the server 120 to provide authorization for the purpose of client 110 or its user's use, access, or management of information. Expressed roles and rules may be established for client 110 or the user of client 110 such that these characteristics are considered or ignored in the provision of authorization to information using a determined relationship context.

The information viewer 140 may accept plug-ins. For example, an extension may be a plug-in and the extension may allow specific types of components of documents to be viewed or otherwise manipulated (e.g., printed, copied and pasted, exported, and the like). As another example, a plug-in may perform optical character recognition of image files in the information viewer 140.

The client 110 or information viewer 140 may restrict use, access, or management of information (either partially or completely) on the basis of explicit or implicit roles, rules, and/or relationship context (e.g. established social distance or trust determined as relevant in the process of authorization) determined by the server 120 in the process of authorizing either the client 110 or the user of client 110 to requested information.

In some implementations, the client 110 may be used to manage access rights, including usage rights or conditions of usage. Managing of access rights may include adding or removing relationships, and editing attributes of relationships such as, adding or removing access or usage rights associated with a relationship, changing conditions for access or usage rights, and the like. Management of some relationships may be restricted to different party roles of the system 100. For example, a data content subject might be able to add a relationship such that a doctor may access or use their health information; yet, the data content subject might not be able to remove their relationship to an insurance company or employer.

The server 120 may receive requests from the client 110 for information or access to information and may use the search tool 170 to find relationships or attributes of relationships to assist in responding to the requests. For example, the client 110 may request access to a medical record of a data content subject and a relationship between a data content recipient and the data content subject may indicate that access to the record may be granted, and, that relationship may be used to grant access to the record by the server 120 (as, for example, is described in reference to FIG. 2).

The relationship repository 125 of relationships and attributes associated with relationships includes one or more data structures for storing relationships among principals and classes of principals recognized by the relationship repository 125. For example, the relationships may include user to user, organization to organization, user to organization, or organization to user relationships. Additional, fewer, or different types of relationships may be included, as well. A combination of relationships specified in the relationship repository 125 may be used to infer an indirect relationship. For example, a relationship between a first user and an organization and a relationship between that organization and a second user may be used to infer an indirect relationship between the first and the second user. A user, as used in reference to types of relationships, may have any of the party roles described above, such as a data content subject.

The relationship repository 125 may be stored in one or more data structures, such as one or more tables, but may also be implemented by generating references within the nodes of a hierarchical data structure that are capable of traversal, configuration or computer-based and/or network-based resources external to the relationship repository 125, or a combination of mechanism, techniques, or both. Advantageously, the use of relationships may allow for a graph-based view of principals (e.g., users, organizations, or systems having roles or accounts with respect to the computer-based resources). For example, a user may belong to multiple organizations by having multiple relationships where the organizations are parents. For example, a user may have multiple employers being parents in multiple relationships.

Having multiple parents may assist in having records of users that exist beyond an existence of a relationship. For example, a user may have a relationship with a past employer and a relationship with a current employer. In some contexts, such as a healthcare environment, having information about past and current relationships may be helpful. For example, if a user switches insurance companies past and present relationships may be used to find information about a user to provide a more complete clinical or administrative history.

Different types of characteristics, which may also be referred to as attributes, may be associated with a relationship. For example, in implementations involving use of relationships to determine access rights, attributes may include a time interval of a relationship, types of content authorized for a relationship, types of authorized access, and the like.

Although the system 100 of FIG. 1 includes a certain combination of features, additional, different, or fewer features may be included. For example, the relationship repository 125 may include relationships but need not include attributes of relationships. As another example, client 110 may be a remote network interface and server 120 may be the gateway to a network of computers or computer systems to which the authentication and authorization of a user of client 110 may provide broader access.

FIG. 2 is a diagram of a system 200 to provide access and usage rights to computer-based resources based on relationship context. The access and usage rights may be based on role, rule, relationship, or any combination of contexts established for principals of the system 200. The system 200 includes a client 210, a server 220, secure documents 230, a credential server 205, a relationship repository 225, a secure document generation server 215, an information repository 235, and a log repository 250.

In general, in the system 200, information from the information repository 235 may be secured as secure information in a component of a secure document or a secure document such that the client 210 may only perform actions with the information (e.g., a component of a secure document or an entire secure document) after being authenticated and obtaining authorization from the server 220, where that authorization is based on a combination of explicit roles, relationships (e.g., an existence of a relationship or attributes of a relationship; e.g., between a data content recipient and a data content subject), or rules governing the use, access, or management of the requested resource. From the generation of secure information to its viewing, the sequence may be as follows. Information from the information repository 235 may be packaged and secured in a secure document by the secure document generation server 215 in accordance with a specification for organizing the information and a policy of maintaining security (e.g., terms and conditions). A policy or policies for organizing the information and maintaining security may be determined by preferences of a data content owner or data content subject as identified by a query of the credential server 205 (e.g., based on preferences associated with a relationship of a data content subject and data content recipient).

Figure 3:
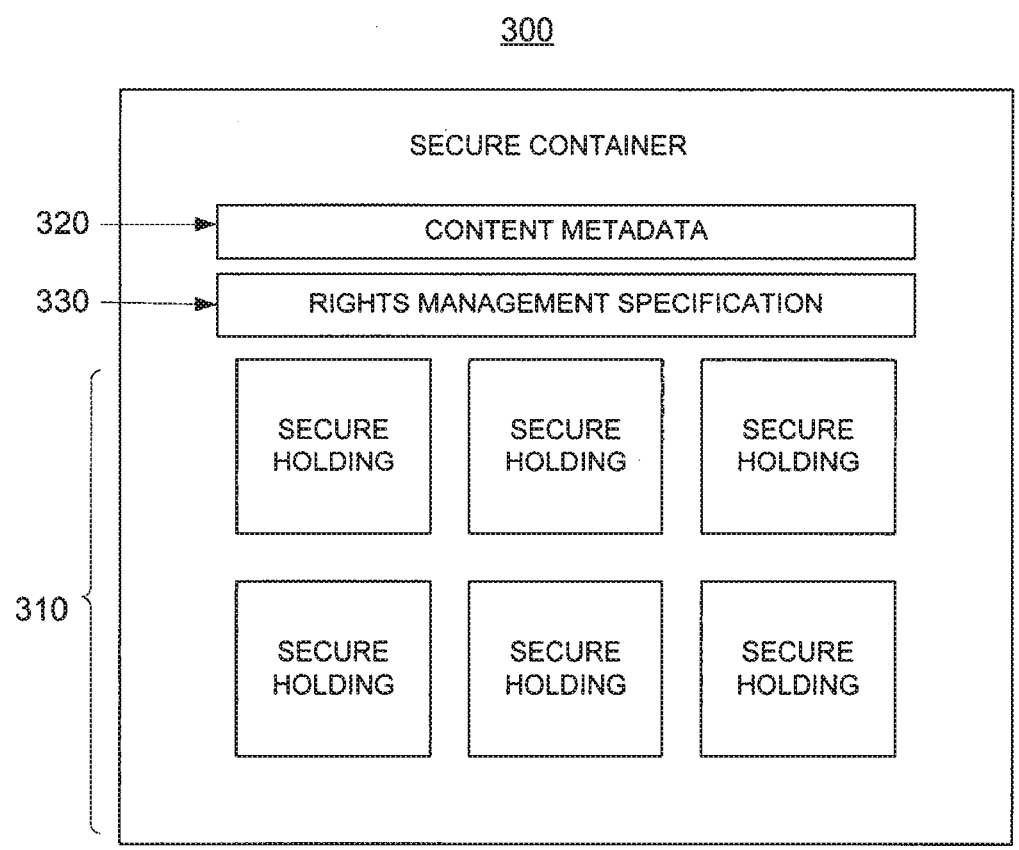
FIG. 3 is a diagram of a structure for a secure document.

In general, a secure document may be a secure container for computer-based resources, such as information or content, such as a secure container structure 300 of FIG. 3 and each of the components of a secure document may be one of secure holdings 310, which contain computer-based resources. Components of the secure documents at the repository 230 may be electronic documents or references to resources, such as electronic documents. For example, components of secure documents may include such computer-based resources, or content, such as audio, image, binary, and text files; these types of content and other computer-based resources, either singularly or in the aggregate may be collectively referred to as a computer files or documents. As another example, a reference to a computer-based resource, such as a uniform resource indicator (URI), may be encrypted in a component of the secure document, the component may be decrypted, and the uniform resource indicator may be used to download and access the computer-based resource referred to by the uniform resource indicator.

The client 210 may allow for access and usage of components of secure documents of the repository 230.

The client 210 may request information from a website 280, which requests information from the secure document generation server 215. The client 210 may be authorized for downloading of information by the website 280, which receives secure documents or components of secure documents from the secure document generation server 215. In some implementations, the secure document generation server 215 need not publish back to the website 280. For example, secure documents or components of secure documents may be sent to a user in an electronic mail message, published to the repository 230 of secure documents (which, for example, may be shared by multiple clients), and the like. In some implementations, a principal need not use the client 210 to request information from the website 280 (e.g., the requesting of information and its viewing need not be combined features of the client 210).

As an example of the client 210 requesting information, the website 280 may receive credentials, such as a user name and password, from the client 210. Alternatively, also as example, a principal may request content directly from the website 280 without presenting credentials. In either case of using 270 as either an authenticated or unauthenticated principal, if the principal is authorized, the information may be downloaded. Following the example, the website 280 may contact the secure document generation server 215 for information. The secure document generation server 215 may contact the credential server 205 with the credentials to determine whether the user of the client 210 is authenticated and whether the principal is authorized to access information by checking the relationship repository 225, which may include a list of users, credentials, and information that may be used to determine whether a principal is authorized to access specific information (e.g., a table of relationships between a data content recipient and a data content subject with attributes describing access rights based on the relationships). If the principal is authorized, the secure document generation server 215 may receive from the credential server 205 a policy of usage of the information (e.g., terms and conditions to be packaged with the information) and policy of generating the data (e.g., specification of a format for the data; e.g., a layout or specification of filtering of data).

The information that is requested by a potential data content recipient (e.g., role of a principal receiving or intended to receive information) need not have a one to one cardinality between a data content subject and a data content recipient. For example, information may be requested for a number of data content subjects by a single data content recipient. In some cases, content related to multiple data content subjects may be necessarily or, alternatively, for convenience be packaged in a single secure document. For example, panel data that may be distributed in the interest of public health may be requested and that panel data may be based on multiple data content subjects. To accommodate for multiple secure content subjects, the secure document generation server 215 may be able to generate a secure document with components that respect terms and conditions of use associated with each of the multiple data content subjects (e.g., a variety of policies may specify different terms and conditions for different data content subjects, and terms and conditions of those policies may be embedded in a secure document and adhered to by the client 210).

Terms and conditions may be derived via attributes associated with principals associated with the roles of data content subjects, data content owners, data content custodians, data content publishers, and the like, or attributes and characteristics associated with relationships associated with those principals as well as implicit or explicit rule-based derivations specified by any combination of roles, rules, and relationship characteristics. Similarly, where the secure document generation server 215 is providing information in a format other than the secure document format, role, rule, or relationship context may apply to one or more parcels of information provided and the authorization for access, management, or use of that information.

Policies for packaging of information may depend on a data content recipient (e.g., for a recipient of a certain insurance company in Massachusetts, insurance companies in Massachusetts may have certain requirements different from other states or that company may have preferences that differ from other companies), relationship of data content subject and data content recipient, and the like. The secure document generation server 215 may package the information in accordance with policies explicitly or implicitly determined by the credential server 205 (e.g., determined as a result of deterministic or probabilistic analysis of principal relationships stored in relationship repository 225). Then, the user of the client 210 may download the information as part of a secure document. In some implementations, access for downloading of information may be restricted and the secure document generation server 215 may contact the credential server 205 to determine whether information may be downloaded by an authorized principal or accessed by an authorized principal using the client 210.

To view or otherwise access or use the information, the client 210 may request authorization from the server 220 by sending credentials for the principal, and the secure information as a component of a secure document or a secure document (e.g., from the repository 230). Then, the server 220 may determine the principal of the client 210 is authenticated based on the credentials via verification process with the credential server 205, the server 220 may determine whether the user of the client 210 is authorized to access the information based on communication with the credential server 205, and, the server 220 may decrypt the information and send the information to the client 210. The credential server 205 may use the relationship repository 225 as part of this process. For example, the credential server 205 may use credentials to authenticate a user and relationships of the user at the relationship repository 225 may be used to determine whether the user is authorized to access the information. For example, an existence of a relationship may indicate authorization, or attributes of a relationship may indicate authorization.

Authentication of user may be a function of client 210 or a function of server 220. Authentication of user may occur each time the client 210 makes a request for access or usage from the server 220. Credentials need not be presented each time a request for content is made. For example, authentication may be provided for a duration, such as a duration of a secure server session. As another example, client 210 or server 220 may cache credentials as a component of a set of interactions with the user.

Credentials may be used to gain access to features or resources of client 210 or server 220, other than secure documents. For example, credentials may provide access to additional menu features of the client. For example, credentials may provide additional information to be generated by the server 220 to be passed back to the client. A user of client 210 may be authenticated at the client, but not authenticated at the server. A user of server 220 may be authenticated at the server, but not authenticated at the client. The credentials provided by a user to the client 210 may be communicated to the server 220, such that relationships in relationship repository 225 may provide the basis for the issuing of additional or improved credentials, or the revoking of existing credentials to the user.

The repository 230 may be shared among a number of potential recipients (e.g., a file server, and the like), shared between a number of potential recipients and data content subjects (e.g., a mobile phone, personal digital assistant, UNIVERSAL SERIAL BUS drive, and the like), or represent the attachment of the secure format to another secure or insecure format (e.g., as an email attachment, a multimedia mobile message service communication, network message, peer-to-peer computing communication, and the like).

If the client 210 is authorized to access or use the information, the server 220 may enable access or use at the client 210. For example, the server 220 may decrypt secure information and send the information to the client 210 in accordance with another security. Enabling access at the client 210 may include sending to the client 210 a version of a secure document having first type of security removed in lieu of a second type of security that can be removed by the client 210.

To send the information to the client 210, the server 220 may secure the information in accordance with a session key negotiated with the client 210 or using other techniques or mechanisms that enable the client 210 to access the information.

In implementations involving different types of access and usage rights, the server 220 may receive an indication of a type of access or usage requested and the server 220 may approve or deny a specific action.

Types of access and usage rights may depend on a user of the client 210 (e.g., different access and usage rights may be associated with different relationships of data content recipients and a data content subject), and the client 210 may enforce those access and usage rights and prevent unauthorized access. In some implementations, access and usage rights may be restricted based on terms and conditions of a secure document or component of secure document that are included in a secure document. Access and usage rights may also be restricted based on capabilities of the client 210 to provide security or reliably restrict access or use by a data content recipient. In addition, the terms and conditions may differ depending on a role of a data content recipient. For example, a system that accesses information as the client 210 may have a role as a research institution, and terms and conditions for usage of the information may be enforced based on that role (e.g., terms and conditions may differ across different roles). For users having multiple roles, different conflict resolution procedures may be adhered (e.g., a broadest or most restrictive set of terms and conditions may be adhered).

In some implementations, the process of the server 220 may generally be viewed as moving information from a first trusted environment (e.g., information as it is secure from the secure document generation server 215) to a second trusted environment (e.g., a secure server session) by removing a first security and adding a second security. The server 220 may also remove first security and add a second security for reasons other than changing trusted environments, including updating security with a type of security considered more secure, updating security with a type of security of varying strength or algorithm characteristic, or updating security with security supported with credentials that are issued to replace credentials that have expired with regard to previous security (e.g., a different set of credentials to be used to decrypt components of secure documents), or changing security as may be necessitated for distribution of content (e.g., for security supported by another platform).

The first security and the second security may use same or different techniques, mechanism, or a combination of the two. For example, the first security may use a same encryption technique as the second security but may require different credentials. As another example, the secure documents of the repository 230 may be encrypted using a first security technique and the security tool 275 may be used to remove the encryption. Then, the security tool 275 may use a second type of security, such as a secure server session between the client 210 and server 220 to send the secure document or part of the secure document to the client 210. Advantageously, the first security of secure documents might only be removable at the server 220 to enhance security of the secure documents and the computer-based resources they contain (e.g., to avoid having to send a cryptographic private key to the client 210 to decrypt secure documents, which might jeopardize a trusted use of that private key, should the key be intercepted or otherwise obtained by an unauthorized party).

As an example of implementations in a health care environment, electronic medical records of a data subject may be stored in an encrypted format at the repository 230 of a data recipient. The data recipient may request access from the server 220 to view a medical record through the client 210 by sending credentials, the medical record, and a requested type of access to the server 220. Based on the credentials authenticating the user of the client 210 and authorization based on a attributes associated with a relationship of the user, the server 220 may decrypt the record and re-encrypt the record in accordance with a session key negotiated with the client 210. The record, encrypted with the session key, and access rights for the record may be sent back to the client 210 by the server 220. Then, the client 110 may allow usage of the record in accordance with the requested action. Access and usage of the record may be in accordance with terms and conditions specified in the secure document, or the component of the secure document. In some implementations, components of a secure document, rather than an entire secure document, may be requested for access, sent to the server 220, and decrypted.

The client 210 may allow for different types of access of secure documents of the repository 230. The types of access may include viewing, copying (e.g., copying and pasting of text, screen captures, export of data, and the like), modifying, printing, and the like. The client 210 includes an information viewer 240. The information viewer 240 may present documents to a user for which the client 210 has access rights and allow for types of access other than viewing to be performed depending on access rights granted to the client 210. For example, a user of the client 210 may be prevented from any type of access, in which case, a document might not be viewable. As another example, a user of the client 210 may be allowed to view and print documents, but, might not be allowed to copy or modify documents.

To ensure enforcement of access and usage rights, the client 210 may be required to be a trusted client. For example, the client 210 may be authenticated by the server 220 as a client that ensures enforcement. For example, the client 210 may send authentication information to the server 220 to indicate the client 210 is a proper client for authorizing access or use of secure documents. For example, client 210 may be proprietary to ensure enforcement of security (and, prevention of unauthorized access) or may be certified as following a specification for clients (or, client environments). For example, the client 210 may be a tool in a suite of software tools that make up an application and the tool may be certified as a client complying with a specification for security enforcement. As another example, the client 210 may be a suite of software tools or programming interfaces that ensure enforcement of access and usage rights.

The client 210 may request access rights from the server 220 by, as examples, establishing a secure server session, sending an application to application message, and the like. The request may include different types of information. For example, a request may include metadata for a document and a secure version of the document. In addition to metadata, other information may include, as example, a version of the client 210 or a component of the secure document (e.g., requested for access), cryptographic key specifications (e.g., a reference or description of a key used for the component), or cryptography algorithms enforced or required for document security and access/use.

Advantageously, including a document as part of a request may allow for distributed storage of documents and may facilitate transport of documents, as the server 220 need not store secure documents and users need not contact the server 220 to receive documents (e.g., secure, encrypted documents may be transferred or accessed via electronic mail, a UNIVERSAL SERIAL BUS-compliant memory key, mobile phone, personal digital assistant, and the like). In addition, the document may be signed (e.g., cryptographically signed) such that the client 210 or server 220 may authenticate the document (e.g., to indicate a document has not been altered). In some implementations, to reduce network bandwidth consumption or unnecessary storage by data content recipients, secure documents or portions of secure documents may be cached or stored at the server 220 and a request from client 210 may simply identify a secure document or portion of a secure document to be accessed without including that content along with user credentials and proposed action for usage at client 210, such that the secure document or portion of secure document, which may be accessible only to server 220, may have first security removed and second security added, and secure document or portion of secure document with second security is sent back to client 210.

The information viewer 240 of the client 210 may allow for exploring of secure documents or parts of secure documents of the repository 230. For example, a user of the client 210 may browse a list of secure documents and may select a secure document to view, which may cause the information viewer 240 to request access for viewing the selected secure document. The repository 230 may be remote (i.e. not proximal) from the client 210 such that secure documents or secure document parts may be accessed by browsed using protocols including FTP (File Transfer Protocol), WebDAV (Web Distributed Authoring And Versioning), HTTP/SHTTP (HyperText Transfer Protocol/Secure HyperText Transfer Protocol), and the like. The client 210 may be embedded in other application or called by another application as a plug-in or helper to assist with the content type associated with the secure document or component of secure document type used for communication between client 210 and server 220 in a specific computing or operating environment. This association may occur by mechanisms including Internet Engineering Taskforce (IETF) specification compliant MIME (Multipurpose Internet Mail Extensions) type or operating system extension.

To allow for management of secure documents before access and usage rights have been granted, some metadata of the secure documents may be viewed. For example, a name of a computer-based resource stored as a component of a secure document or a short description of that component of a secure document might be used and need not be secured from viewing by a user who has not been authenticated or authorized.

The server 220 may authorize access and use of secure documents of the repository 230 by authenticating a user with an authentication tool 260, authorizing the user, and by removing security of a document with a security tool 275. In addition to removing security, the security tool 275 may be used to apply security to the document. For example, a user may request access to a document by sending a request from the client 210 to the server 220 and the server 220 may authenticate the user of the client 210 with the authentication tool 260. Then, if authenticated and authorized, the security tool 275 may be used to remove the security from a secure document, and, the document may be sent to the client 210 with a different, second security for the document. This second security may be specific to the client 210, the user of client 210, or negotiated as a characteristic of the specific use or request.

The packaging and securing of information by the secure document generation server 215 may occur in response to a request for information from the client 210 or in response to other stimulus. For example, in a medical environment, a doctor may request results of an exam and that information may be packaged in a particular format and secured at the secure document generation server 215. Documents may be encrypted using a cryptographic public key that corresponds to a cryptographic private key that is necessary for decryption at the server 220. In some implementations, any number or types of security may be applied at the secure document generation server 215. Different types of security may have different strengths (e.g., one cryptographic algorithm may be inherently stronger than another, or alternatively the same cryptographic algorithm may be made stronger by altering the keys or other inputs to the algorithm used). The format for generating a secure document may be the format described with reference to FIG. 3 and preferences of the format of information of the holdings may be determined with reference to policies provided by the credential server 205. In some implementations, a number of formats may be supported (e.g., for different systems that use different formats). Many different types of information may be in the information repository 235. For example, in a health care environment, the information may include insurance claims, bills, x-rays, test results, signed waivers, doctor observations, a medical history summary, and the like.

Any number of secure document generation servers may be deployed for distributed secure document generation. For example, in a health care environment, a number of secure document generation servers may be distributed across different insurance companies and hospitals for generating secure versions of their respective information.

Information in the information repository 235 need not be packaged and secured document format. Information in the information repository 235 may be governed by a file system or other mechanism that recognizes authorization of the user of client 210 or client 210 as condition to govern the use, management, or access to its information. The information repository 235 may represent a logical construct, such as a virtual file system.

To deal with updates to data, changes may be required to be performed at a source, such that a secure document generation server, such as the secure document generation server 215, packages and secures updated data. Once changes have been made, access to secure documents in circulation may be disabled (e.g., a request of the server 220 to view a secure document or component of the secure document may be denied) and parties seeking access to changed information may be notified that updates may be retrieved. In some implementations, status or awareness of updates may be published. For example, the secure document generation server 215 may publish updates to the client 220 or the website 280.

In general, the credential server 205 manages polices for access and usage of information, including specifications or policies of packaging of information in secure documents, such as in accordance with the structure 300 of FIG. 3, and usage of secure documents. In addition, the credential server 205 may manage authentication and authorization of users (e.g., users of the website 280 or users who make requests for usage through the server 220 may be authenticated by the credential server 205 using combinations of security information managed by the credential server 205, and, e.g., the credential server 205 may issue credentials to the client 220). For example, the credential server 205 may provide for specification of preferences (e.g., preferences for terms and conditions of a secure document) and relationships (e.g., relationships among users and users, organizations and users, organizations and users, and organizations and organizations), in addition to generation, distribution, and revocation of policies (e.g., policies for generation of a secure document or terms and conditions of a secure document) and digital credentials. For example, the secure document generation server 215 may retrieve necessary key information from the credential server 205 to package a secure container that may take the form of a secure electronic health record according to a specification that has been predefined with an insurance company for that specific insurance group. For example, different states or different companies may have different requirements for providing access or use of content to data content recipients, necessitating that generation of secure documents to be used as secure electronic health records may need to differ depending on the location of the data content subject's primary residence or the place where a data content recipient (e.g., a physician) is providing care such that content of a secure electronic health record is required. For example, policy preferences, such as a duration or location of access, may be part of terms and conditions of usage of information that are provided by the credential server 205.

The credential server 205 may use a relationship repository 225 to store information about individuals, organizations, and relationships, in addition to information about those individuals, organizations, and relationships. For example, a relationship between an insured party and an insurance company may be stored with preferences for access and usage of patient information of the insured party by the insurance company. For example, a relationship between a patient and a research institution may indicate that the research institution may view some types of medical information but not others (e.g., some types of secure holdings but not others). The relationship repository 225 may be implemented as a hierarchical or relational directory, identity management repository, or custom repository or product where individual and organization references are associated with credentials for access to resources and other attributes.

Attributes may include types of access and usage rights for a relationship (e.g., view, print, copy, modify, and the like), access and usage conditions (e.g., restricting viewing by Internet Protocol address, a geography defined by an Internet Protocol address, a time period (e.g., authorization may be valid for ninety days), and the like), types of authorized information (e.g., in a health care environment claims information may be authorized for view by an insurance company but not a research institution), roles (e.g., in a health care environment, a data content recipient having a doctor role may have different access and usage rights than a data content recipient being a hospital administrator), or some combination of the above or other attributes.

Relationship repository 225 may be implemented using a hierarchical data structure, such that it may convey the limitations of storing relationships that relationship repository 225 is intended to resolve.

Additional relationships stored in relationship repository 225 may be expressed in a second, non-hierarchical data structure, multiple non-hierarchical data structures, or multiple hierarchical data structures, or combination of any of the aforementioned techniques. Additional relationships do not need to be stored in the same relationship repository 225, in which case integration (e.g., local or remote integration) may be responsible for brokering requests among multiple relationship repositories 225, aggregating responses to facilitate processing. Multiple responses may not be necessary to determine relationships.

Different types of attributes may be associated with a relationship. For example, in implementations involving use of relationships to determine access rights, attributes may include a time interval of a relationship, types of content authorized for a relationship, types of authorized access, and the like.

There may be different types of relationships and a type of relationship or set of relationships may be characterized as a profile, where a profile may characterize a collection relationships, or a collection of relationships and their associated attributes, a collection of relationships and their associated attributes with predefined values, or a collection of attributes, or a collection of attributes with predefined values. For example, a same combination of parties may have multiple profiles for a relationship, which may be expressed as multiple relationships each having a different set of associated attributes, a single relationship having multiple associated profiles (e.g., as attributes), or a combination of the two techniques. As another example, a profile may be a template of parameters of attributes for relationships.

Profiles may be assigned different types of attributes, including all attributes associated with a relationship. For example, in implementations involving the use of profiles to characterize relationships that may be used to determine access rights, profile attributes may include a time interval of a profile, types of content authorized for a profile, types of authorized access, and the like.

In constructing a relationship, a user may chose among pre-specified profiles to select one that is applicable to serve as the starting template for a relationship, at which point a new instance of a relationship may be generated from that profile and customizations applied may be saved to that relationship or to the profile used in that relationship's generation, or both.

Profiles may be created by explicit or implicit specification. For example, a user may create a profile type to be applied when asserting relationships with doctors, but also, a profile type may be created by the computer application for the user on the basis of how it is observed the user typically specified relationships with doctors.

Profiles may be shared among users. Profiles may be stored as a data structure, in the relationship repository 225. Profiles may be offered as features of a software program and made available to users on a basis of user demographic information, articulated relationships, or state of residence.

Profiles may be restricted for purpose of creating a relationship by the specification of one or more rules that may constrain the use of that profile. For example, it may be illegal for a patient to restrict a doctor from accessing a specific type of information if either the patient or the doctor is resident or providing or receiving care in a given jurisdiction; in this case, a profile creating such a restriction would be inapplicable to the relationship between the patient and the doctor.

To determine whether access and usage rights are allowed for a relationship, information about a component of a secure document (e.g., information about a secure holding) may be used to classify the component such that it may be compared against attributes (e.g., metadata of a secure holding may indicate the holding includes claims information and an attribute of a relationship may indicate access and usage of the claims information is allowed).

In alternative implementations, access and usage rights need not be based on relationships between parties. For example, data content recipients may be associated with information that has access and usage rights attributes. In general, preferences for access of information may be based on a component level (e.g., in the structure 300 of FIG. 3, on the granularity of a secure holding, such as a classification of secure holdings).

Although relationships are discussed as being principal to principal relationships, relationships between parties may be based on profiles, stored as preferences of a principal in relationship repository 225, or using other techniques, mechanisms, or both. As another example, default preferences of a data content subject or the preferences of their relationships may also be used to determine outcomes for authorization. For example, a patient need not have an expressed relationship regarding an ability to provide access to treatment eligibility information, but a relationship between a patient's employer and the patient's current insurance company may have specified a setting for the patient's authorization of this information by default.

Parties included in relationships may include principals, and principals may include the client 210, server 220, credential server 205, and secure document generation server 215.

In scenarios involving a denial of access by the credential server 205, the credential server 205 may process a request for authorization (e.g., from a data content subject or data content custodian). Such a request may be forwarded to a data content subject or data content custodian, such that authorization may be permitted by user interaction. For example, a text message stating that a doctor is requesting access to a certain type of medical data may request a response for authorization being yes or no. Additional policies may be generated in response to such a request or may be considered a one-time exception to typical authorization processing. For example, a new relationship may be generated at the relationship repository 225 and that relationship may include attributes authorizing the data content recipient.

In general, secure documents of the repository 230 are secured to prevent access and use of their information. For example, each component of the secure document may be encrypted using an encryption scheme and the client 210 might not have a decryption engine, resources, or necessary credentials to decrypt the documents. To access the information of the documents, as described above, the server 220 may replace security of the documents with a security that can be removed by the client 210 (e.g., as a form of granting access). In some implementations, multiple clients may share a same authentication and security tool of the server 220. For example, multiple clients may request access to a component of a secure document from the server 220, each client 210 receiving access to that component using a negotiated second security that is different from the first security, but unique to itself, such that information may be accessed. Separate credentials presented by client 210 to server 220 on behalf of a specific user of client 210 may be used as criteria by which a negotiated second security that allows access to information of a secure document may be obtained.

The server 220 may maintain a log of events in the log repository 250. Different events may be logged. For example, the log may include an entry for each access, or attempted access, to a document by a client. Logged events may include varying granularities of detail. To ensure security of a log, the log may be encrypted, not include information that may easily be used to identify a person or company of which information is logged, or a combination of techniques and mechanisms may be implemented.

A log may be used to monitor access to and use of secure documents, parts of secure documents, or components of those parts that may assist ensuring security. For example, a data content subject may review log access to information distributed in secure documents to be assured that unauthorized users have not accessed that information. In a health care environment, some users may be required to monitor medical information and a log may be used as a compliance verification tool to determine if someone is monitoring information. Logging may include both accesses that are approved and denied. In some implementations, logging of approvals may include limited information whereas denials may include detailed information (e.g., to assist in showing a policy prevented access to information). For example, an entry of an approval may include metadata about information approved and a data content recipient, whereas a denial may further include a description of a policy of a user (e.g., a policy of a relationship of a data content subject and data content recipient) that led to a denial. The log may be viewed by, as examples, a user of the website 280 (e.g., to data content subjects, data content recipients, data content custodians, and the like) or a system administrator of the server 220. Authorization to view the log may be provided based on attributes associated relationships in the relationship repository 225 (e.g., and governed by the credential server 205).

Logging may include details of user operations other than access with respect to client 210 and server 220. For example, changes to access rights, such as an addition of a relationship, may be logged. As another example, system downtime may be logged. Logging may include details of allowed or denied operations that relate to actors other than the client 210 and the server 220. Access to log may also be controlled by a user authorization. Access to individual components of log information may be controlled by user authorization or attributes associated with a principal.

Contents or changes to a log may be distributed, or accessed as part of a secure or otherwise distributed communication to authorized parties that may have interest or requirements to observe the log and its changes. For example, a log may be distributed across different portions of one or more computer systems. As another example, updates about access to a patient's medical history may be communicated to the patient in the form of a secure document, an electronic mail notification, a text message, and the like. Similarly, for example, access to a patient's treatment eligibility or coverage information may be communicated to that patient's insurance company or payer, such that the organization may be notified of a potential opportunity to investigate an incident that may be of interest.

As another example, the secure document generation server 215 need not provide information in a specific format. Information to supplement the generation of a secure document may be stored independently of a secure document. For example, metadata about a secure document may be collected and used independently of the secure document from which it is derived.

Although FIG. 2 provides an example system 200 where role, rule, or relationship context-based authorization may be implemented, similar techniques, mechanisms, or both may be featured in varying implementations. Similarly, although the system 200 of FIG. 2 includes a certain number and type of components, implementations may differ. For example, a number of clients, secure document generation servers, and servers may exist. As another example, components need not be associated as depicted in FIG. 2.

As another example, the client 210 may have credentials in addition to user credentials by which the server may establish trust of the client 210 (e.g., code signing of the client), such that the server 220 is able to verify that the client 210 adheres to established standards for governing user access and usage to data by the articulated authorization policy granted by the server 220.

As another example, an interface for providing access or usage of data to a user need not be a website, such as the website 280 and the interface of the client 210 may differ. For example, a suite of web-accessible services, such as services that might be accessed via SMS (Short Message Service), MMS (Multimedia Messaging Service), or IVR (Interactive Voice Response) system may be provided. The services may be exposed by an underlying application programming interface that may communicate with the secure document generation server 215, the credential server 205, and the server 220. The client 210, as examples, may be a mobile phone that accepts and composes text messages, a telephone, personal data assistant, and the like.

As another example, the secure document generation server 215 need not generate a secure document. For example, the secure document generation server 215 may act as a proxy for the integration of data, or the integration of data as a secure document. For example, the secure document generation server 215 may act as proxy to integrate data that does not become a secure document by integrating metadata from multiple sources that results in an aggregation of metadata, which may assist in generating secure documents or responding to other types of requests.

As another example, the hosting and granularity of features may differ. For example, the server 220, the website 280, and the credential server 205 may be hosted at a same site, different sites, or some combination of hosting may be performed. Similarly, the hosting of repositories need not be paired with servers and intermediate components may exist. For example, the relationship repository 225 need not be paired with the credential server 205 and a server may be used to interface with the relationship repository 225.

As another example, the information repository 235 need not be paired with the secure document generation server (e.g., located nearby). For example, the information repository 235 may reside on one or more servers remote from the secure document generation server 215. As another example, the secure document generation server 215 need not contact the information repository 235 directly to receive information. For example, data communicated between information repository 235 and secure document generation server 215 may be the product of an ETML (Extraction, Transformation, Move, and Load) process that occurs synchronously or asynchronously across multiple information repositories or as the result of data-layer integration, process-layer integration, or service-layer integration established among zero or more computer systems identified as providing required information. As another example, a component may act as a data broker, and the data broker may include a tool that facilitates synchronous or asynchronous ETML; or data-level, process-level, or service-level integration between the secure document generation server 215 and the information repository 235 where the data broker allows for aggregation and integration of information remote from the secure document generation server 215.

Although FIGS. 1 and 2 include a separation between a client 110, 210 and a server 120, 220, such a division need not exist. In general, the terms client and server may refer to client and server application programs, although, they may refer to client and server computer systems. A client and server are generally remote from each other and typically interact through a communication network; however, a client and server need not have a dedicated connection. The relationship of client and server may arise by virtue of one computer program, referred to as a server, providing a service to another computer program, referred to as a client. The servers 220, 120 may be referred to as a "clearing server," and a combination of the credential server 205 and the server 220 may be referred to as a "policy server," "identity management tool," or "policy management tool."

FIG. 3 is a diagram of a structure 300 for a secure document. The structure 300 may be referred to as a secure container and includes the secure holdings 310, metadata 320, and a rights management specification 330. The structure 300 may be a structure of the secure documents of the repository 230 of system 200 of FIG. 2. For example, the secure documents or components of secure documents of the repository 230 of FIG. 2 may include one of the secure holdings 310 or portions of the secure holdings 310. For example, in a healthcare environment the structure 300 may be a secure electronic health record of a data subject and each of the secure holdings 310 may be portions of a health record, such as a set of test results, an x-ray image, and the like.

The secure holdings 310 are components of the structure 300 and each of them may be secure from access. For example, each of the secure holdings 310 may be encrypted. Each of the secure holdings 310 may have separate types of security or require separate credentials; a uniform type of security may be applied to the secure holdings 310; or some commonality of security may exist. For example, in health care environment, claims may be secured using a same protocol for their secure holdings while a different security protocol may be used for secure holdings of medical results, such as x-rays. In some implementations, the secure holdings 310 may include other information. For example, terms and conditions of use of content of the secure holdings 310 may be encrypted with each of the secure holdings 310. For example, terms and conditions may include a specification requiring the use of a specific issuing root public key certificate that is trusted to facilitate clearing of the content. Each of the secure holdings 310 may further include a unique identifier that allows the secure holdings 310 to be tracked, along with the structure 300 that was used at the time the structure 300 was constructed.

The metadata 320 may include information about the structure 300 and the secure holdings. In particular, the metadata 320 may include an index of the secure holdings 310 in the structure 300 and a general description of the structure 300. For example, in a health care environment, the metadata 320 may include non-sensitive biographical information about a patient and short descriptions of secure holdings 310 that may be searched on the basis of non-sensitive diagnosis and procedure codes. For example, information identifying a data content subject in one of the systems 100, 200 of FIGS. 1, 2 may be included without identifying an individual outside of the system (e.g., an identifier of a patient used in the systems 100, 200 but not related to a social security number), and that information may be used to identify the data content subject when determining whether a data content recipient is authorized to view secure holdings.

The rights management specification 330 may include a specification of data from a secure document generation server, such as the secure document generation server 215, that details security for the secure holdings 310. For example, in the healthcare environment, information about the building of a secure electronic health record may be included. In addition, information for a client to access the secure holdings may be included in the rights management specification 330. For example, information identifying a location of a server for providing authorization, which may be referred to as a clearing server, and a specification of roles and credentials that are eligible for requesting content access. The rights management specification 330 may be articulated in a declarative format (e.g., Request For Comments 822 compliant file, eXtensible Markup Language dialect, runtime compiled scripting language, and the like) or programmatic format (e.g., application programming interface, and the like) used by a programmatic subsystem that encrypts data to generate a secure container.

Although the structure of FIG. 3 includes a certain number and type of features, additional, fewer, or different features may be included. For example, the rights management specification 330 may be combined with the metadata 320.

As another example, although FIG. 3 shows a first level of nesting of secure holdings 310 of the structure 300, there may be any number of levels of nesting of sub-components or sub-holdings. For example, a secure holding may have multiple secure sub-holdings. The secure sub-holdings themselves may be documents that are separately encrypted or an entire secure holding of a secure document may be encrypted. The security applied to sub-holdings may either be dependent or independent of the security applied to the secure holding of which it is apart. Similarly, different terms and conditions may be applied to different secure sub-holdings of the secure holding of a secure document. For example, in the generation of a secure document to reflect population-specific information, content for multiple data content subjects may be organized into individual sub-holdings of a parent secure holding that represents a specific classification of population information (e.g., diagnosis or disease identification information) while each secure sub-holding is independently governed by access and usage policies appropriate for each respective data content subject.

Although the structure of FIG. 3 includes a certain number and type of features, additional, fewer, or different features may be included. For example, the rights management specification 330 may be combined with the metadata 320.

Figure 4:
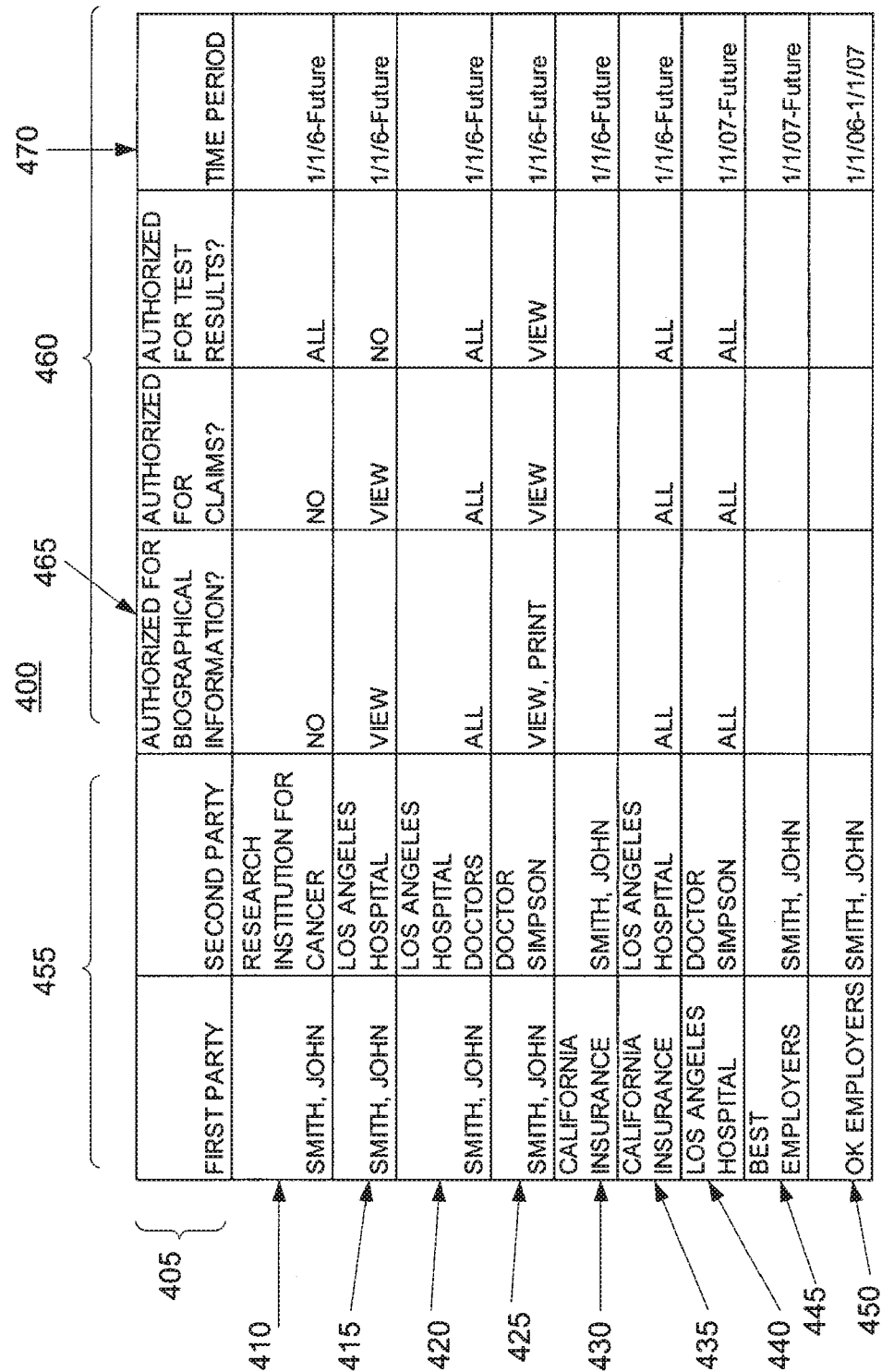
FIG. 4 is a diagram of a structure of a table of relationships and associated attributes.

FIG. 4 is a diagram of a structure of a table 400 of relationships and associated attributes. The table 400 may be part of the relationship repository 125 FIG. 1 or the relationship repository 225 of FIG. 2. In general, the table 400 includes headings 405 describing columns of the table 400 and table entries 410-450.

For each of the entries 410-450, a pair of first and second party identification is used to describe a relationship between the first and second party, where the first party may represent a parent node and the second party may represent a child node of the parent node in a graph of relationships (e.g., a directed graph). For example, the first entry 410 includes a first party John Smith and a second party Research Institution for Cancer, where John Smith may be considered the parent of Research Institution for Cancer. The parties of the table 400 may be principals, as discussed above.

The parties included in the first and second party columns 455 may include users and organizations, such that a combination of the columns may represent user to user, user to organization, organization to user, and organization to organization relationships. Attributes of relationships may be included in columns 460 associated with a relationship. For example, attributes of a row are associated with a relationship in that row defined by the first and second party columns 455. For example, a second entry 410 describes that a relationship between John Smith and Los Angeles Hospital is associated with authorization to view biographical information.

The attributes of relationships in the table 400 include access rights associated with a relationship and a temporal attribute of a relationship. For example, some of the attributes in columns 460 describe types of access allowed for a child of a parent, for a type of content in each of the columns 460. For example, a first attribute 465 of a fourth entry 410 describes that Doctor Simpson may only view and print biographical information of John Smith. As an example of a temporal attribute, the temporal attribute 470 that the relationship between OK Employers (e.g., a name of a company) and John Smith lasted from Jan. 1, 2006 to Jan. 1, 2007. A combination of attributes of a relationship may be referred to as a policy for a relationship.

The relationships specified in the table 400 may be used to determine indirect relationships among parties. For example, the relationship between John Smith and Los Angeles Hospital in the second entry 415 may indicate that Los Angeles Hospital has access rights to John Smith's records, the relationship between Los Angeles Hospital and Doctor Simpson may indicate that Doctor Simpson inherits the access rights of Los Angeles Hospital. In combination, the relationships may indicate that Doctor Simpson may access records of John Smith by virtue of the relationships with Los Angeles Hospital.

Different techniques may be used to resolve conflicts among relationships and identify attributes that should be used. For example, explicit, direct relationships may override implicit, indirect relationships. For example, the indirect relationship of Doctor Simpson and John Smith by virtue of their relationships with Los Angeles Hospital may be overridden by the explicit, direct relationship Between John Smith and Doctor Simpson in the fourth entry 425. Consequently, the attributes of the fourth entry 425 may be used for their relationship. In some implementations, to ensure a greater availability of information, attributes having less-restrictive access rights may override more restrictive access rights. In some implementations, a special scenario, such as emergency care in the health care environment, may override attributes of a relationship.

Relationships, their attributes, or both may be managed by a data content subject, data custodian, system administrator, and the like. For example, a user may desire that they do not wish to be affiliated with a hospital and may change attributes to revoke access or usage of their patient information from employees of the hospital. As another example, a relationship between an employer and employee may be generated by a system administrator and the request of an employer.

The table 400 illustrates how a user or organization may have relationships that reflect having multiple parents. For example, two entries 445, 450 include relationships between employers and John Smith, indicating different employers for different periods of time, according to the temporal attribute 470, where each of the employers, OK Employers and Best Employers are considered parents. Thus, a "many to many" cardinality of party relationships may exist, and some may include temporal distinctions.

Relationships that may be considered static or dynamic may be stored in the table 400. For example, organization to user and organization to organization relationships may be considered static, and user to organization or user to user relationships may be considered dynamic. For example, relationships that are considered static may include an insurance company and insured party, as such a relationship is not believed to change often. As another example, relationships between data content subjects and data content recipients may be considered dynamic as a data content subject may change such a relationship often.

While some relationships of the table 400 may indicate a data content recipient's access rights inherited from another party (e.g., from a data content subject or data content custodian), other types of relationships may be reflected. For example, where null attributes (e.g., no value or a zero value) are included for access rights, such as a fifth entry 430 between California Insurance and John Smith, the null attributes may indicate that relationships of the first party, or parent, may be used to find a relationship to the second party, or child. For example, the relationship of the fifth entry 430 may indicate that John Smith has all the relationships of California Insurance. For example, if John Smith does not otherwise have a relationship with a hospital named San Diego Hospital but California Insurance does, the access rights of that relationship may be used to determine access rights for content of John Smith to San Diego Hospital.

Although FIG. 4 uses the table 400 to define relationships and related attributes, other types of data structures may be used. In some implementations, another data structure, such as another table, may be used in addition to the table 400 of FIG. 4 to define relationships or attributes of a user or organization. For example, another table may define attributes of users or organizations. For example, secure containers associated with a data content subject, whether an organization or user may be available in another table and the relationships of table 400 may be used to determine whether a data content recipient has access rights to content about the data content subject. For example, in an environment using the secure container structure of FIG. 3, a user may have an attribute for each secure holding and each attribute may include a unique identifier of such a holding, and the unique identifier may be used by a secure document generation server, such as the secure document generation server 215 of FIG. 2, to generate a secure holding which may be downloaded.

Although table 400 includes a certain type and organization of information, implementations may vary. For example, fewer, additional or different attributes may be associated with a relationship. For example, attributes may further include a geography or Internet Protocol address for restricting content associated with a relationship (e.g., only doctors within a city may have access and usage of content of a certain patient; or, only computers accessing or using data within an Internet Protocol domain of a hospital may access or use content).

In some implementations, attributes of a relationship may describe a nature of a relationship. And, a same combination of parties may have multiple entries, where entries have different types of relationships. Also, part of an association may be a child type code, reference identifier code, and reference identifier code type. In that example, the child type code may represent a type of child that the parent would consider this type of child to be in a traditional directory server's organization unit structure (e.g., in an employer to employee relationship). The reference identifier code and reference identifier code type may permit multiple identification codes for a given relationship. For example, an insurance company may have a parent-child relationship with an employer, where the relationship is captured by both an internal employer identification that is used for claims remission and reimbursement and a federal tax identification number that is used for the purpose of maintaining contracts.

Figure 5:
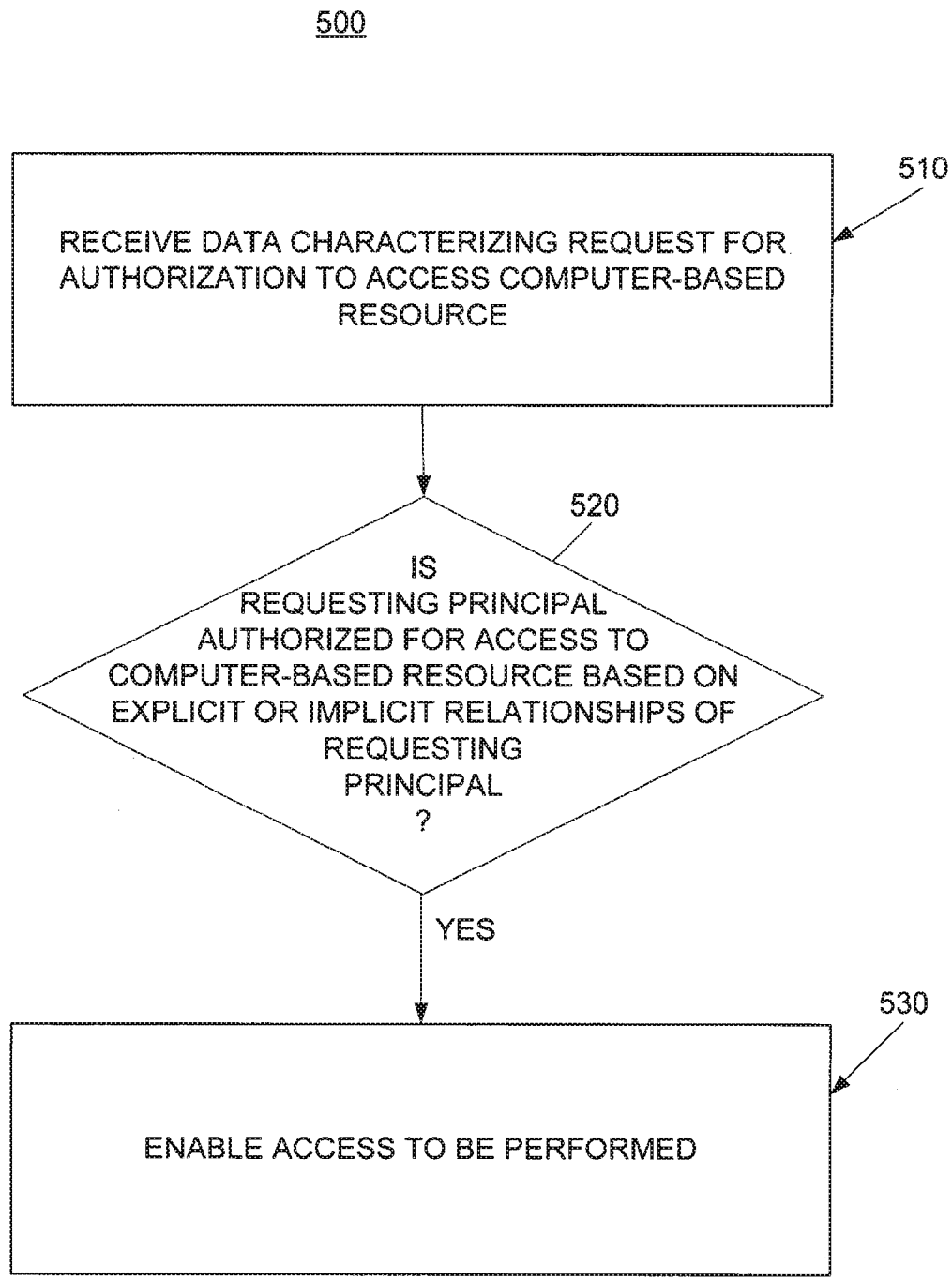
FIG. 5 is a flowchart illustrating a process of providing relationship-based access to computer-based resources.

FIG. 5 is a flowchart illustrating a process of providing relationship-based access to computer-based resources. The process 500 may use the table 400 of FIG. 4, the structure 300 of FIG. 3, the system 200 of FIG. 2, or a combination of components. In general, the process 500 involves receiving a request for authorization to access a computer-based resource, determining whether a relationship exists between a requesting principal and a principal related to the computer-based resource from which access may be granted (e.g., a data content subject), and, enabling access if a relationship exists (and, e.g., if attributes of a relationship indicate authorization).

Data characterizing a request for authorization to access a computer-based resource may be received (510). The data may be received at a server to respond to requests for access to computer-based resources, such as the server 220 of FIG. 2. In some implementations that request may be for computer-based resources, rather than access to computer-based resources. The request may originate and be fulfilled by a same principal. For example, a server, such as the server 220, may be a principal and the server may manage authorization. The request may have been generated by a client attempting to access secure computer-based resources, such as the client 210 of FIG. 2 that requests secure information. The data characterizing the request may be a message including a secure computer-based resource and metadata for the secure computer-based resource. For example, a secure holding of a medical record may be sent with an identifier of a data content subject. The request may be generated by a principal, which may be a user of a client or part of a program. For example, a request may be generated when a program attempts to access a secure computer-based resource as part of performing a task that uses the computer-based resource. The request may include a type of access requested. In some implementations, a request need not include a secure computer based resource as a request. For example, a request may only involve the presentation of credentials, URIs (e.g., a URI of a requested computer-based resource), process identifiers, or some combination of that information.

A determination is made as to whether a requesting principal is authorized for access to a computer-based resource based on relationships of a requesting principal (520). For example, the request may be based on explicit relationships, implicit relationships, or both of a requesting principal. For example, whether the relationships are with a principal for which an existence of relationship or attributes of a relationship may indicate authorization is to be granted. For example, the determination may involve determining whether a requesting principal has an explicit relationship with a principal being a user or organization from which access may be granted. For example, determining whether the table 400 of FIG. 4 includes a relationship between a requesting principal and a data content subject (e.g., of the computer-based resource being requested). As another example, the determination may include determining whether a relationship between a requesting principal and a data content subject may be implied from a combination of multiple relationships. For example, a combination of a relationship of a hospital to a doctor, where the doctor is a requesting principal, and a relationship of a data content subject and the hospital may be combined to imply a relationship between the data content subject and the doctor.

In some implementations, the determination may involve determining whether attributes associated with a relationship authorize access. In addition, the determination may involve determining which types of access are authorized.

If a requesting principal is authorized, access may be enabled to be performed (530). For example, a version of a computer-based resource with security replaced or removed may be sent to a requesting principal of the client 210 of FIG. 2.

For example, first credentials may be used to identify an account of a data content recipient. Metadata of a secure document that is sent with a request to access the document may be used to determine an account of the data content subject. Then, a table of relationships may be queried to determine if the data content subject and data content recipient have a direct or indirect relationship. If a relationship does not exist, the data content recipient might not be granted access. If a relationship does exist, the relationship may include access right preferences that may be used to determine access rights to grant to a data content recipient (e.g., a principal attempting to access computer-based resource), and the data content recipient may be granted access rights. The security of the secure document may be removed in accordance with second credentials.

In addition to removing security in accordance with the second security credentials, other types of security may be added. For example, the server 220 of FIG. 2 may decrypt a document using a private key and then encrypt the document using a session key negotiated for a secure server session. The purpose of having such a combination of removing security in lieu of other security may move a secure document from a first trusted environment to a second trusted environment. In addition, by preventing security of a transportable container from being removable at a client, security may be improved. For example, a client need not receive a key that may be used at any computer to decrypt an easily transportable version of the document, which may prevent exposure of security mechanisms; and, exposure of a session key of a single document that is expected to be in a second trusted environment for the length of a session might be considered a less significant security risk.

Although attributes associated with a relationship may be checked to approve or deny a specific type of access or types of accesses, in some implementations, transmission of the computer-based resource may also include a specification of rights to be adhered to by a requestor. For example, access right and usage preferences, such as access rights authorizing viewing and printing but not copying a computer-based resource may be sent to the client 110 and enforced by the client 110.

Although FIG. 5 has a certain combination of sub-processes in a certain order, additional, fewer, or different sub-processes may be used and the order may differ. For example, the process 500 may be adapted for the system 100 of FIG. 1. For example, the request may be a request for information as a type of computer-based resource. As another example, criteria other explicit and implicit relationships may be used to determine whether a requesting principal is to be authorized.

In some implementations, authentication of a requesting user may be performed. Different types of relationships may exist among a same pair of parties. For example, a user may have a relationship with a hospital for when a user is a patient of the hospital and the user may also have a relationship where the user is an administrator of the hospital. Different types of relationships may be used to determine whether access is authorized. Following the previous example, a relationship of an administrator of a hospital may be combined with other relationships to determine access rights of computer-based resources about patients other than the administrator, but, the relationship of a user as a patient of the hospital might not be used to determine access rights to computer-based resources about other users.

Other information about a user may be used to determine access rights. For example, a data content recipient may be associated with one or more roles, such as doctor role, administrator role, and the like, which may define a granularity of access rights for an organization. For example, if a data content subject has a relationship with a hospital, doctors of the hospital having a doctor role may have more access rights than administrative staff of the hospital having an administrative role.

Although FIGS. 1-5 are discussed with references to examples in a healthcare environment, similar techniques and/or mechanisms may be employed in other environments.

A user, as discussed with reference to FIGS. 1-5 generally refers to a person who manipulates an input device to interact with a computer; however, the term user need not be so limited (e.g., a principal). For example, a user may be a computer program that acts as a user. For example, the client 110 of FIG. 1 may be used by a program and such a client may include, for example, an application programming interface in lieu of a graphical user interface.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, i.e., one or more computer programs tangibly embodied in an information carrier, e.g., in a machine-readable storage device or in a propagated signal, for execution by, or to control the operation of, data processing apparatus, e.g., a programmable processor, a computer, or multiple computers. A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other in a logical sense and typically interact through a communication network. The relationship of client and server arises by virtue of computer programs running on the respective computers and having a client-server relationship to each other.

The subject matter described herein has been described in terms of particular embodiments, but other embodiments can be implemented and are within the scope of the following claims. For example, operations can differ and still achieve desirable results. In certain implementations, multitasking and parallel processing may be preferable. Other embodiments are within the scope of the following claims

What is claimed is:

1. A non-transitory computer program product, tangibly embodied in a computer-readable media, the computer program product comprising instructions configured to cause at least one data processor forming part of at least one computing system to perform operations comprising:
   receiving data characterizing a request for authorization to access a computer-based resource by a principal;
   determining whether the requesting principal is authorized for the access to the computer-based resource based on a context of the request, the determining occurring using a relationship repository comprising one or more data structure containing relationships, the data structures being separate and non-referential from the computer-based resource, the determining comprising:
      determining whether the requesting principal has an explicit relationship at the time of the request with a principal that has management rights of access to the computer-based resource, wherein the explicit relationship includes at least one of a user to user relationship, a user to organization relationship, and an organization to organization relationship; and
      determining whether the relationship allows for the access to the computer-based resource if the requesting principal has a relationship with the principal that has management rights; otherwise, determining whether an organization of the requesting principal has a relationship, with the principal that has management rights, that allows for the access; and
   providing authorization for the requesting principal to the computer-based resource.

2. The computer program product of claim 1, wherein the principal is a user, organization, computer system, or component of a computer system.

3. The computer program product of claim 1, wherein the relationships are stored in a table such that a graph of relationships is described, the graph comprising at least one child node of relationships having a plurality of parent nodes.

4. The computer program product of claim 1, wherein the determining whether the requesting principal has a relationship with a principal and determining whether an organization of the requesting principal has a relationship with the principal that has management rights are performed with reference to one or more data structures describing relationships between users and users, users and organizations, organizations and users, and organizations and organizations.

5. The computer program product of claim 1, wherein the principal having management rights is a data content subject about whom the computer-based resource relates.

6. The computer program product of claim 1, wherein the requesting principal has a relationship with the principal having management rights at a first time to authorize the access but the relationship at a second time being later than the first time does not authorize the access based on a modification of the relationship or associated attributes.

7. The computer program product of claim 1, wherein relationships are associated with one or more attributes.

8. The computer program product of claim 7, wherein at least one of the attributes describes one or more of a time interval of a relationship, types of computer-based resources authorized for a relationship, or types of authorized access.

9. The computer program product of claim 1, wherein the receiving data and the determining whether the requesting principal is authorized are performed at a server and the operations further comprise performing the access at a client.

10. The computer program product of claim 1, wherein the request is a request for access to clinical or administrative health information in a health care environment.

11. The computer program product of claim 1, wherein the requesting principal is authorized for types of access to the computer-based resources different from types of access authorized for another principal.

12. A computer-implemented method comprising:
   receiving data characterizing a request for authorization to access a computer-based resource by a principal;
   determining whether the requesting principal is authorized for the access to the computer-based resource based on a context of the request, the determining occurring using a relationship repository comprising one or more data structures containing relationships, the data structures being separate and non-referential from the computer-based resource, the determining comprising:
      determining whether the requesting principal has an explicit relationship at the time of the request with a principal that has management rights of access to the computer-based resource, wherein the explicit relationship includes at least one of a user to user relationship, a user to organization relationship, and an organization to organization relationship; and determining whether the relationship allows for the access to the computer-based resource if the requesting principal has a relationship with the principal that has management rights; otherwise, determining whether an organization of the requesting principal has a relationship, with the principal that has management rights, that allows for the access; and providing authorization for the requesting principal to the computer-based resource.

13. The method of claim 12, wherein the relationships are stored in a table such that a graph of relationships is described, the graph comprising at least one child node of relationships having a plurality of parent nodes.

14. The method of claim 12, wherein the determining whether the requesting principal has a relationship with a principal and determining whether an organization of the requesting principal has a relationship with the principal that has management rights are performed with reference to one or more data structures describing relationships between users and users, users and organizations, organizations and users, and organizations and organizations.

15. The method of claim 12, wherein relationships are associated with one or more attributes describing one or more of a time interval of a relationship, types of computer-based resources authorized for a relationship, or types of authorized access.

16. The method of claim 12, wherein the request is a request for access to health information in a health care environment.

17. A non-transitory computer program product, tangibly embodied in a computer-readable media, the computer program product comprising instructions configured to cause at least one data processor forming part of at least one computing system to perform operations comprising:

receiving data characterizing a request for access to a computer-based resource by a first principal;

determining whether the first principal is authorized for the access to the computer-based resource, the determining occurring using a relationship repository comprising one or more data structures containing relationships, the data structures being separate and non-referential from the computer-based resource, the determining comprising:

determining whether the first principal has a first relationship at the time of the request with a second principal that has management rights of access to the computer-based resource, the determining whether the first principal has the first relationship with the second principal based on a query of one or more data structures comprising user to user relationships between principals being users; and determining whether the first relationship allows for the access to the computer-based resource based on properties of the first relationship if the first principal has the first relationship; otherwise, determining whether an organization of the first principal has a second relationship, with the second principal, that allows for the access, the determining whether the organization has the second relationship based on user to organization relationships and organization to user relationships of the data structures; and providing authorization for the requesting principal to the computer-based resource.

18. The computer program product of claim 17, wherein the relationships are stored in a table such that a graph of relationships is described, the graph comprising at least one child node of relationships having a plurality of parent nodes.

19. The computer program product of claim 17, wherein the request is a request for access to health information in a health care environment.

20. The computer program product of claim 17, wherein the data structures are one or more tables.

21. The computer program product of claim 1, wherein the explicit relationship has been verified through a trusted third party.

22. The method of claim 12, wherein the explicit relationship has been verified through a trusted third party.

23. The computer program product of claim 17, wherein the relationship between the first principal and second principal is verified through the trusted third party.

24. The computer program product of claim 1, wherein the relationship repository is secured by a trusted third party.

25. The method of claim 12, wherein the relationship repository is secured by a trusted third party.

26. The computer program product of claim 17, wherein the relationship repository is secured by a trusted third party.

* * * * *